(12) United States Patent
Saiki et al.

(10) Patent No.: US 10,066,080 B2
(45) Date of Patent: Sep. 4, 2018

(54) RUBBER COMPOSITION, TIRE, BISANILINO COMPOUND, AND ANTI-AGING AGENT

(71) Applicant: OTSUKA CHEMICAL CO., LTD., Osaka-shi, Osaka (JP)

(72) Inventors: Aya Saiki, Kunitachi (JP); Hidehiro Minashima, Kodaira (JP); Yuzaburo Yano, Kodaira (JP); Noriaki Shiina, Osaka (JP); Kazuhiro Kodama, Osaka (JP); Mifuyu Ueno, Osaka (JP); Takashi Sato, Osaka (JP); Shinya Nakashima, Osaka (JP); Masaki Abe, Osaka (JP)

(73) Assignee: OTSUKA CHEMICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/312,801

(22) PCT Filed: May 22, 2015

(86) PCT No.: PCT/JP2015/002600
§ 371 (c)(1),
(2) Date: Nov. 21, 2016

(87) PCT Pub. No.: WO2015/178039
PCT Pub. Date: Nov. 26, 2015

(65) Prior Publication Data
US 2017/0166728 A1 Jun. 15, 2017

(30) Foreign Application Priority Data

May 22, 2014 (JP) .................................. 2014-106398

(51) Int. Cl.
| | |
|---|---|
| *C08K 5/00* | (2006.01) |
| *C08K 5/20* | (2006.01) |
| *C08L 9/00* | (2006.01) |
| *B60C 1/00* | (2006.01) |
| *C07C 237/04* | (2006.01) |
| *C07C 321/14* | (2006.01) |
| *C07C 211/55* | (2006.01) |
| *C07C 217/08* | (2006.01) |
| *C07C 235/16* | (2006.01) |
| *C07D 295/13* | (2006.01) |

(Continued)

(52) U.S. Cl.
CPC .............. *C08K 5/20* (2013.01); *B60C 1/0016* (2013.01); *B60C 1/0025* (2013.01); *C07C 211/55* (2013.01); *C07C 217/08* (2013.01); *C07C 235/16* (2013.01); *C07C 237/04* (2013.01); *C07C 321/14* (2013.01); *C07D 295/13* (2013.01); *C08K 5/3462* (2013.01); *C08K 5/375* (2013.01)

(58) Field of Classification Search
CPC .. C08K 5/005; C08K 5/20; C08K 5/29; C08L 9/00
See application file for complete search history.

(56) References Cited

U.S. PATENT DOCUMENTS

| | | | | |
|---|---|---|---|---|
| 3,975,414 A | * | 8/1976 | Kline .................... | C08K 5/3725 524/217 |
| 4,633,016 A | * | 12/1986 | Buysch ................ | C08K 5/3725 560/25 |
| 6,365,653 B1 | * | 4/2002 | Meier .................... | C07C 317/44 524/155 |

FOREIGN PATENT DOCUMENTS

| | | | |
|---|---|---|---|
| EP | 310 140 A2 * | 4/1989 | ........... C07C 149/20 |
| EP | 0310140 A2 | 4/1989 | |
| EP | 0916695 A1 | 5/1999 | |

(Continued)

OTHER PUBLICATIONS

Kim, H.; Kim, T.-G.; Park, J.-W. Macromolecular Research 2013, 21(7), 815-820.*

(Continued)

*Primary Examiner* — Rip A Lee
(74) *Attorney, Agent, or Firm* — Kenja IP Law PC

(57) ABSTRACT

Provided is a rubber composition that contains at least one rubber component selected from natural rubber and diene-based synthetic rubbers and, blended therewith, at least one bisanilino compound represented by formula (I). In formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom, a sulfur atom, or an —$NR^3$— group, and $X^2$ represents an oxygen atom, a sulfur atom, or an —$NR^4$— group, where $R^3$ and $R^4$ each represent a hydrogen atom or an alkyl group having a carbon number of 1-4, or collectively form an alkylene group having a carbon number of 1-4.

7 Claims, No Drawings

(51) Int. Cl.
*C08K 5/375* (2006.01)
*C08K 5/3462* (2006.01)

(56) References Cited

FOREIGN PATENT DOCUMENTS

| | | |
|---|---|---|
| JP | H0892370 A | 4/1996 |
| JP | 2005232355 A | 9/2005 |
| JP | 2010509415 A | 3/2010 |
| JP | 2010536952 A | 12/2010 |
| JP | 2013155259 A | 8/2013 |

OTHER PUBLICATIONS

Gao, J.; Li, K.; Zhang, W.; Wu, Z.; Jing, F.; MacDiarmid, A.G. Polymer Preprints 1998, 39(2), 532.*

Sep. 27, 2017, Extended European Search Report issued by the European Patent Office in the corresponding European Patent Application No. 15796710.0.
Nov. 13, 2017, Office Action issued by the State Intellectual Property Office in the corresponding Chinese Patent Application No. 201580026681.1.
Nov. 22, 2016, International Preliminary Report on Patentability issued in the International Patent Application No. PCT/JP2015/002600.
Jun. 30, 2015, International Search Report issued in the International Patent Application No. PCT/JP2015/002600.
Mar. 6, 2018, Notification of Reasons for Refusal issued by the Japan Patent Office in the corresponding Japanese Patent Application No. 2014-106398.
Jun. 6, 2018, Office Action issued by the State Intellectual Property Office in the corresponding Chinese Patent Application No. 201580026681.1.

* cited by examiner

RUBBER COMPOSITION, TIRE, BISANILINO COMPOUND, AND ANTI-AGING AGENT

TECHNICAL FIELD

The present disclosure relates to a rubber composition, a tire, a bisanilino compound, and an anti-aging agent, and, in particular, relates to a rubber composition that is suitable for use in tread rubber or sidewall rubber of a tire.

BACKGROUND

Rubber articles having natural rubber or a diene-based synthetic rubber as a raw material generally deteriorate over time and suffer from crack formation at the surface thereof when exposed to an environment in which ozone is present. Such cracks propagate as the rubber article is subjected to static stress and dynamic stress, and may eventually result in rupturing of the rubber article.

In order to prevent and inhibit the formation and propagation of cracks in a rubber article due to ozone, particularly in the case of tread rubber or sidewall rubber of a tire, it has become common practice to use a rubber composition that contains an amine-based anti-aging agent such as N-(1,3-dimethylbutyl)-N'-phenyl-p-phenylenediamine (PTL 1 and 2).

CITATION LIST

Patent Literature

PTL 1: JP 2010-509415 A
PTL 2: JP 2010-536952 A

SUMMARY

Technical Problem

However, when an amine-based anti-aging agent such as described above is used in a rubber article, the external appearance of the rubber article may deteriorate as a consequence of the anti-aging agent having a high tendency to migrate to the surface of the rubber over time, leading to discoloration and staining of the rubber surface by what is referred to as "blooming".

In recent years, there has been demand for improvement of rubber article weather resistance, such as ozone resistance. Particularly in the case of tire production, strategies are being adopted for reducing the gauge thickness of various tire members in order to provide better fuel efficiency and conserve resources. Under these circumstances, there is demand for a rubber composition that has even better weather resistance than a conventional rubber composition containing an amine-based anti-aging agent such as described above.

Therefore, one objective of the present disclosure is to provide a rubber composition that has better weather resistance than conventional rubber compositions and can inhibit surface discoloration of a rubber article. Another objective of the present disclosure is to provide a tire that has superior weather resistance and in which rubber article surface discoloration is inhibited.

Solution to Problem

The inventors conducted diligent investigation in order to achieve the objectives described above, resulting in the discovery that a rubber composition that has superior weather resistance and that can inhibit surface discoloration of a rubber article can be obtained through blending of a compound having a specific structure with a rubber component. This discovery led to the present disclosure.

Specifically, a presently disclosed rubber composition comprises at least one rubber component selected from natural rubber and diene-based synthetic rubbers and, blended therewith, at least one bisanilino compound represented by formula (I) shown below

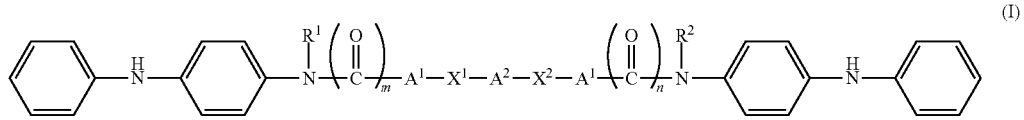

where, in formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom, a sulfur atom, or an —$NR^3$— group, and $X^2$ represents an oxygen atom, a sulfur atom, or an —$NR^4$— group, where $R^3$ and $R^4$ each represent a hydrogen atom or an alkyl group having a carbon number of 1-4, or collectively form an alkylene group having a carbon number of 1-4. As a result of the presently disclosed rubber composition containing the aforementioned bisanilino compound as an anti-aging agent, weather resistance of the presently disclosed rubber composition can be significantly improved compared to conventional rubber compositions and surface discoloration of a rubber article can be inhibited.

From a viewpoint of sufficiently improving weather resistance and preventing discoloration, it is preferable that in the bisanilino compound represented by formula (I) that is contained in the presently disclosed rubber composition, $R^1$ and $R^2$ are each, independently of one another, an alkyl group having a carbon number of 3-6, m and n are each 0, $A^1$ is an alkylene group having a carbon number of 1-4, $A^2$ is an alkylene group having a carbon number of 5-8, and $X^1$ and $X^2$ are each an oxygen atom.

In the presently disclosed rubber composition, a blending amount of the bisanilino compound represented by formula (I) is preferably in a range of from 0.2 parts by mass to 10 parts by mass relative to 100 parts by mass of the rubber component. As a result of the blending amount of the bisanilino compound being in the range described above, it is possible to sufficiently improve weather resistance and inhibit discoloration while also restricting the amount of the bisanilino compound that is consumed.

A presently disclosed tire comprises a tire member in which the above-described rubber composition is used. The aforementioned tire member is preferably either or both of a tread and a sidewall. The presently disclosed tire has superior weather resistance and rubber article surface discoloration is inhibited therein.

A presently disclosed bisanilino compound is represented by formula (I) shown below

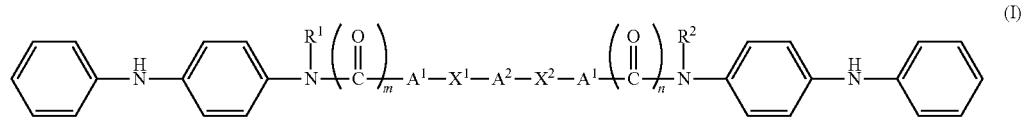

(I)

where, in formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom, a sulfur atom, or an —$NR^3$— group, and $X^2$ represents an oxygen atom, a sulfur atom, or an —$NR^4$— group, where $R^3$ and $R^4$ each represent a hydrogen atom or an alkyl group having a carbon number of 1-4, or collectively form an alkylene group having a carbon number of 1-4. A presently disclosed anti-aging agent for natural rubber and diene-based synthetic rubber-use comprises the above-described bisanilino compound.

Advantageous Effect

According to the present disclosure, it is possible to provide a rubber composition that has better weather resistance than conventional rubber compositions and that can inhibit surface discoloration of a rubber article, and also to provide a tire that has superior weather resistance and in which rubber article surface discoloration is inhibited.

DETAILED DESCRIPTION

<Rubber Composition>

The following provides a detailed description of the present disclosure. A presently disclosed rubber composition contains at least one rubber component selected from natural rubber and diene-based synthetic rubbers and, blended therewith, at least one bisanilino compound represented by formula (I) shown above.

<<Rubber Component>>

Examples of rubber components that can be used in the presently disclosed rubber composition include natural rubber (NR) and diene-based synthetic rubbers such as isoprene rubber (IR), butadiene rubber (BR), and styrene-butadiene copolymer rubber (SBR). One of these rubber components may be used individually, or two or more of these rubber components may be used in combination as necessary.

<<Bisanilino Compound>>

The presently disclosed rubber composition contains at least one bisanilino compound represented by formula (I) shown above. In formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom, a sulfur atom, or an —$NR^3$— group, and $X^2$ represents an oxygen atom, a sulfur atom, or an —$NR^4$— group, where $R^3$ and $R^4$ each represent a hydrogen atom or an alkyl group having a carbon number of 1-4, or collectively form an alkylene group having a carbon number of 1-4.

The bisanilino compound represented by formula (I) that is used in the presently disclosed rubber composition has a high molecular weight compared to conventional anti-aging agents and, as shown in formula (I), includes a bridge moiety having a characteristic and comparatively long chain length section. Specifically, the bisanilino compound represented by formula (I) includes a moiety composed by -$A^1$-$X^1$-$A^2$-$X^2$-$A^1$-. It is thought that as a result of the bisanilino compound having a high molecular weight and including this characteristic bridge moiety, the rate of diffusion of the bisanilino compound within the rubber composition is reduced and, accordingly, migration of the bisanilino compound to the rubber surface is inhibited to a greater extent.

The bisanilino compound represented by formula (I) has an excellent anti-aging effect with respect to rubber components such as natural rubber and diene-based synthetic rubbers, and can be used as an anti-aging agent for rubber component-use.

The following provides a description of the various chemical groups referred to in the present specification.

Examples of alkyl groups having a carbon number of 1-4 include linear, branched, and cyclic alkyl groups having a carbon number of 1-4 such as a methyl group, an ethyl group, an n-propyl group, an isopropyl group, an n-butyl group, an isobutyl group, a sec-butyl group, a tert-butyl group, and a cyclobutyl group.

Examples of alkyl groups having a carbon number of 1-6 include the examples of alkyl groups having a carbon number of 1-4 provided above and other linear, branched, and cyclic alkyl groups having a carbon number of 1-6 such as various pentyl groups, examples of which include an n-pentyl group, an isopentyl group, a neopentyl group, a tert-pentyl group, and a cyclopentyl group; and various hexyl groups, examples of which include an n-hexyl group, an isohexyl group, a 4-methyl-2-pentyl group, and a cyclohexyl group.

Examples of alkyl groups having a carbon number of 3-5 include linear, branched, and cyclic alkyl groups having a carbon number of 3-5 among the examples of alkyl groups having a carbon number of 1-6 provided above.

Examples of alkyl groups having a carbon number of 3-6 include linear, branched, and cyclic alkyl groups having a carbon number of 3-6 among the examples of alkyl groups having a carbon number of 1-6 provided above.

Examples of alkylene groups having a carbon number of 1-3 include linear and branched alkylene groups having a carbon number of 1-3 such as a methylene group, an ethylene group, a trimethylene group, a propylene group, and a dimethylmethylene group.

Examples of alkylene groups having a carbon number of 1-4 include the examples of alkylene groups having a carbon number of 1-3 provided above and other linear and branched alkylene groups having a carbon number of 1-4 such as a 2-methyltrimethylene group and a tetramethylene group.

Examples of alkylene groups having a carbon number of 1-7 include the examples of alkylene groups having a carbon number of 1-4 provided above and other linear and branched alkylene groups having a carbon number of 1-7 such as a pentamethylene group, a 2,2-dimethyltrimethylene group, a hexamethylene group, a 1,4-dimethyltetramethylene group, and a heptamethylene group.

Examples of alkylene groups having a carbon number of 1-8 include the examples of alkylene groups having a carbon number of 1-7 provided above and other linear and branched alkylene groups having a carbon number of 1-8 such as various octamethylene groups.

Examples of alkylene groups having a carbon number of 5-8 include linear and branched alkylene groups having a carbon number of 5-8 among the examples of alkylene groups having a carbon number of 1-8 provided above.

Examples of alkylene groups having a carbon number of 6 or 7 include linear and branched alkylene groups having a carbon number of 6 or 7 among the examples of alkylene groups having a carbon number of 1-8 provided above.

In the bisanilino compound represented by formula (I), $R^1$ and $R^2$ are each, independently of one another, a hydrogen atom or an alkyl group having a carbon number of 1-6. However, from a viewpoint of sufficiently improving weather resistance and preventing discoloration, it is preferable that $R^1$ and $R^2$ are each, independently of one another, an alkyl group having a carbon number of 3-6, and more preferable that $R^1$ and $R^2$ are each, independently of one another, an alkyl group having a carbon number of 3-5.

In the bisanilino compound represented by formula (I), m and n are each an integer of 0 or 1. However, from a viewpoint of sufficiently improving weather resistance and preventing discoloration, m and n are preferably both 0.

In the bisanilino compound represented by formula (I), $A^1$ is an alkylene group having a carbon number of 1-7. However, from a viewpoint of sufficiently improving weather resistance and preventing discoloration, $A^1$ is preferably an alkylene group having a carbon number of 1-4, more preferably an alkylene group having a carbon number of 1-3, and particularly preferably a methylene group or an ethylene group. In the bisanilino compound represented by formula (I), $A^2$ is an alkylene group having a carbon number of 1-8. However, from a viewpoint of sufficiently improving weather resistance and preventing discoloration, $A^2$ is preferably an alkylene group having a carbon number of 5-8 and more preferably an alkylene group having a carbon number of 6 or 7.

In the bisanilino compound represented by formula (I), $X^1$ is an oxygen atom, a sulfur atom, or an —$NR^3$— group and $X^2$ is an oxygen atom, a sulfur atom, or an —$NR^4$— group, where $R^3$ and $R^4$ are each a hydrogen atom or an alkyl group having a carbon number of 1-4, or collectively form an alkylene group having a carbon number of 1-4. Herein, the alkyl group may be a linear, branched, or cyclic alkyl group. It should be noted that in a situation in which $R^3$ and $R^4$ collectively form an alkylene group, a cyclic structure is formed by $X^1$, $A^2$, and $X^2$. From a viewpoint of sufficiently improving weather resistance and preventing discoloration, $X^1$ is preferably an oxygen atom or an —$NR^3$— group and is more preferably an oxygen atom. Moreover, from a viewpoint of sufficiently improving weather resistance and preventing discoloration, $X^2$ is preferably an oxygen atom or an —$NR^4$— group and is more preferably an oxygen atom.

Examples of compounds such as described above include
N,N'-bis(4-anilinophenyl)-3,3'-(hexan-1,6-diyldiimino) dipropaneamide,
N,N'-bis(4-anilinophenyl)-2,2'-[hexan-1,6-diylbis(sulfandiyl)]bisacetamide,
N,N'-bis(4-anilinophenyl)-N,N'-diisopropyl-2,2'-[hexan-1,6-diylbis(sulfandiyl)]bisacetamide,
N,N'-bis[2-(4-anilinoanilino)ethyl]-N,N'-dimethylethane-1,2-diamine,
N,N'-bis{2-[(4-anilinophenyl)(isopropyl)amino]ethyl}-N,N'-dimethylethane-1,2-diamine,
N',N'''-diphenyl-N,N''-[hexan-1,6-diylbis(oxyethylene)]dibenzene-1,4-diamine,
N,N''-diisopropyl-N',N'''-diphenyl-N,N''-[hexan-1,6-diylbis(oxyethylene)]dibenzene-1,4-diamine,
N',N'''-diphenyl-N,N''-[ethylenebis(oxypentan-5,2-diyl)]dibenzene-1,4-diamine,
N,N'-bis(4-anilinophenyl)-N,N'-diisopropyl-2,2'-(butan-1,4-diyldioxy)bisacetamide,
N,N'-bis(4-anilinophenyl)-2,2'-[butan-1,4-diylbis(sulfandiyl)]bisacetamide,
N,N'-bis(4-anilinophenyl)-N,N'-diisopropyl-2,2'-[butan-1,4-diylbis(sulfandiyl)]bisacetamide,
N,N''-diisopropyl-N',N'''-diphenyl-N,N''-(piperazine-1,4-diyldiethylene)dibenzene-1,4-diamine,
N',N'''-diphenyl-N,N''-[2-methylpropan-1,3-diylbis(oxyethylene)]dibenzene-1,4-diamine,
N',N'''-diphenyl-N,N''-[(2,2-dimethylpropan-1,3-diyl)bis(oxyethylene)]dibenzene-1,4-diamine, and
N,N''-diisopropyl-N',N'''-diphenyl-N,N''-[butan-1,4-diylbis(oxyethylene)]dibenzene-1,4-diamine. Of these compounds
N',N'''-diphenyl-N,N''-[hexan-1,6-diylbis(oxyethylene)]dibenzene-1,4-diamine,
N,N''-diisopropyl-N',N'''-diphenyl-N,N''-[hexan-1,6-diylbis(oxyethylene)]dibenzene-1,4-diamine,
N',N'''-diphenyl-N,N''-[ethylenebis(oxypentan-5,2-diyl)]dibenzene-1,4-diamine, and
N',N'''-diphenyl-N,N''-[2-methylpropan-1,3-diylbis(oxyethylene)]dibenzene-1,4-diamine are preferable.

The bisanilino compound represented by formula (I) can be produced by reactions shown below in reaction formulae 1-5.

(Reaction formula 1)

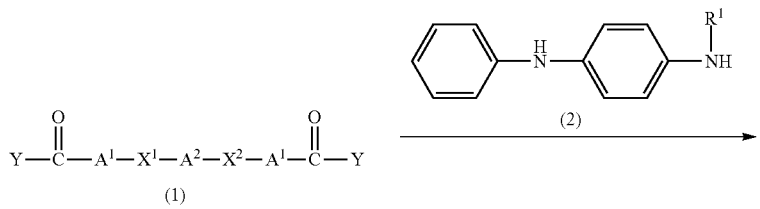

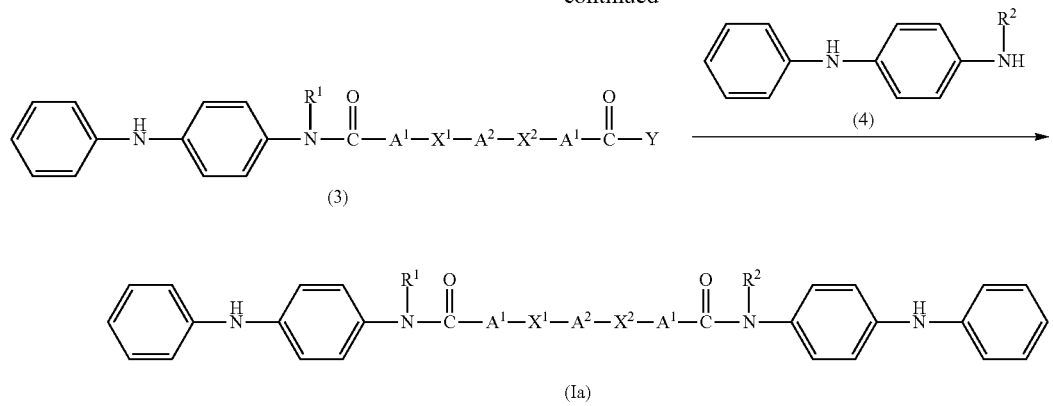

(In reaction formula 1, $R^1$, $R^2$, $A^1$, $A^2$, $X^1$, and $X^2$ are the same as previously described and Y represents a halogen atom.)

According to reaction formula 1, a diamide compound represented by formula (Ia) can be produced by causing an acid halide compound represented by formula (1) to act on an aniline compound represented by formula (2) to produce an amide compound represented by formula (3) and subsequently causing an aniline compound represented by formula (4) to act on the amide compound represented by formula (3) in the same way. The diamide compound represented by formula (Ia) is a compound that is included within the scope of the presently disclosed bisanilino compound represented by formula (I).

Each of the above-described reactions is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; aromatic solvents such as toluene, xylene, and benzene; halogen-containing solvents such as dichloromethane and carbon tetrachloride; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the aniline compound represented by formula (2) or (4) is normally approximately 1 part by mass to 500 parts by mass and preferably approximately 5 parts by mass to 100 parts by mass.

In the reaction in which the acid halide compound represented by formula (1) acts on the aniline compound represented by formula (2), the amount of the aniline compound represented by formula (2) that is caused to react relative to the acid halide compound represented by formula (1) is normally from 0.5 equivalents to 1.2 equivalents and preferably from 0.8 equivalents to 1 equivalent.

In the reaction in which the acid halide compound represented by formula (3) acts on the aniline compound represented by formula (4), the amount of the aniline compound represented by formula (4) that is caused to react relative to the acid halide compound represented by formula (3) is normally from 0.8 equivalents to 2 equivalents and preferably from 1 equivalent to 1.5 equivalents.

In the reaction in which the acid halide compound represented by formula (1) acts on the aniline compound represented by formula (2), an aromatic amine such as pyridine, N,N-dimethyl-4-aminopyridine, pyrazine, or 2,6-lutidine or an aliphatic amine such as trimethylamine, triethylamine, pyrrolidine, piperidine, or piperazine may be used as a base with respect to the acid halide compound represented by formula (1). The amount of such bases that is caused to react relative to the aniline compound represented by formula (2) is normally from 0.5 equivalents to 1.2 equivalents and preferably from 0.8 equivalents to 1 equivalent.

In the reaction in which the acid halide compound represented by formula (3) acts on the aniline compound represented by formula (4), an aromatic amine such as pyridine, N,N-dimethyl-4-aminopyridine, pyrazine, or 2,6-lutidine or an aliphatic amine such as trimethylamine, triethylamine, pyrrolidine, piperidine, or piperazine may be used as a base with respect to the acid halide compound represented by formula (3). The amount of such bases that is caused to react relative to the aniline compound represented by formula (4) is normally from 0.8 equivalents to 2 equivalents and preferably from 1 equivalent to 1.5 equivalents.

Note that in a situation in which the substituents $R^1$ and $R^2$ are the same, the diamide compound represented by formula (Ia) can be produced through a single-step reaction in which at least 2 equivalents of the aniline compound represented by formula (2) is used relative to the acid halide compound represented by formula (1).

The reactions can normally be carried out in a temperature range of from −78° C. to the boiling temperature of the solvent that is used. However, the reactions are normally carried out at approximately −10° C. to 50° C. and preferably at around room temperature.

Although it is not possible to make generalizations about the reaction time since the reaction time varies depending on the reaction temperature and so forth, the reactions are normally completed in approximately 0.5 hours to 24 hours.

(Reaction formula 2)

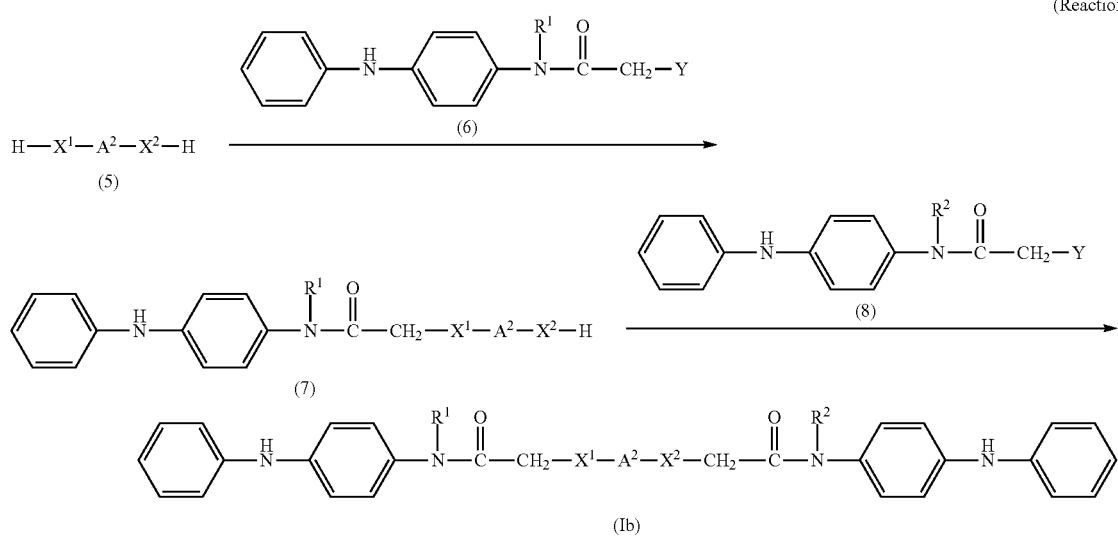

(In reaction formula 2, $R^1$, $R^2$, $A^1$, $A^2$, $X^1$, $X^2$, and Y are the same as previously described.)

According to reaction formula 2, a diamide compound represented by formula (Ib) can be produced by causing a haloacetamide compound represented by formula (6) to act on a compound represented by formula (5) to produce an amide compound represented by formula (7) and subsequently causing the amide compound represented by formula (7) to act on a haloacetamide compound represented by formula (8) in the same way. The diamide compound represented by formula (Ib) is a compound that is included within the scope of the presently disclosed bisanilino compound represented by formula (I).

Each of the above-described reactions is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; aromatic solvents such as toluene, xylene, and benzene; halogen-containing solvents such as dichloromethane and carbon tetrachloride; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the compound represented by formula (5) or the amide compound represented by formula (7) is normally approximately 1 part by mass to 500 parts by mass and preferably approximately 5 parts by mass to 100 parts by mass.

In the reaction in which the haloacetamide compound represented by formula (6) acts on the compound represented by formula (5), the amount of the haloacetamide compound represented by formula (6) that is caused to react relative to the compound represented by formula (5) is normally from 0.5 equivalents to 1.2 equivalents and preferably from 0.8 equivalents to 1 equivalent.

In the reaction in which the haloacetamide compound represented by formula (8) acts on the amide compound represented by formula (7), the amount of the haloacetamide compound represented by formula (8) that is caused to react relative to the amide compound represented by formula (7) is normally from 0.8 equivalents to 2 equivalents and preferably from 1 equivalent to 1.5 equivalents.

In the reaction in which the haloacetamide compound represented by formula (6) acts on the compound represented by formula (5), lithium hydride, sodium hydride, potassium hydride, n-butyllithium, tert-butyllithium, lithium diisopropylamide, lithium hexamethyldisilazide, sodium hexamethyldisilazide, or the like may be used as a base with respect to the compound represented by formula (5). The amount of such bases that is caused to react relative to the compound represented by formula (5) is normally from 0.5 equivalents to 2.2 equivalents and preferably from 0.5 equivalents to 1 equivalent.

In the reaction in which the haloacetamide compound represented by formula (8) acts on the amide compound represented by formula (7), lithium hydride, sodium hydride, potassium hydride, n-butyllithium, tert-butyllithium, lithium diisopropylamide, lithium hexamethyldisilazide, sodium hexamethyldisilazide, or the like may be used as a base with respect to the compound represented by formula (7). The amount of such bases that is caused to react relative to the amide compound represented by formula (7) is normally from 0.5 equivalents to 2.2 equivalents and preferably from 0.5 equivalents to 1 equivalent.

Note that in a situation in which the substituents $R^1$ and $R^2$ are the same, the diamide compound represented by formula (Ib) can be produced through a single-step reaction in which at least 2 equivalents of the haloacetamide compound represented by formula (6) is used relative to the compound represented by formula (5).

The reactions can normally be carried out in a temperature range of from −78° C. to the boiling temperature of the solvent that is used. However, the reactions are normally carried out at approximately −10° C. to 50° C. and preferably at around room temperature.

Although it is not possible to make generalizations about the reaction time since the reaction time varies depending on the reaction temperature and so forth, the reactions are normally completed in approximately 0.5 hours to 24 hours.

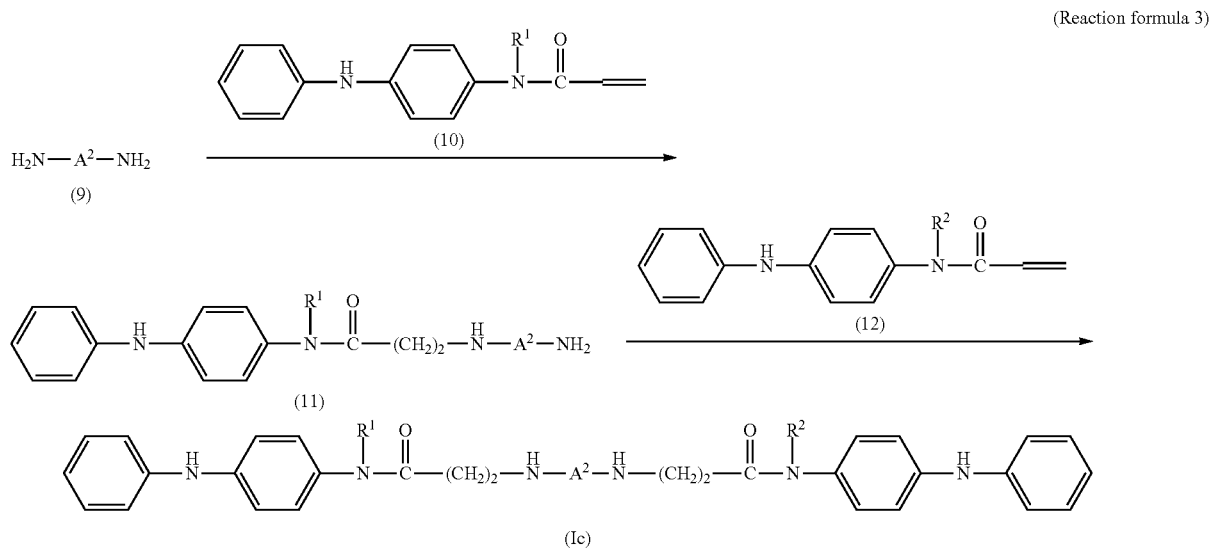

(Reaction formula 3)

(In reaction formula 3, $R^1$, $R^2$, and $A^2$ are the same as previously described.)

According to reaction formula 3, a diamide compound represented by formula (Ic) can be produced by causing an acrylamide compound represented by formula (10) to act on a diamine compound represented by formula (9) to produce an amine compound represented by formula (11) and subsequently causing the amine compound represented by formula (11) to act on an acrylamide compound represented by formula (12) in the same way. The diamide compound represented by formula (Ic) is a compound that is included within the scope of the presently disclosed bisanilino compound represented by formula (I).

Each of the above-described reactions is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; aromatic solvents such as toluene, xylene, and benzene; halogen-containing solvents such as dichloromethane and carbon tetrachloride; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the diamine compound represented by formula (9) or the amine compound represented by formula (11) is normally approximately 1 part by mass to 500 parts by mass and preferably approximately 5 parts by mass to 100 parts by mass.

In the reaction in which the acrylamide compound represented by formula (10) acts on the diamine compound represented by formula (9), the amount of the acrylamide compound represented by formula (10) that is caused to react relative to the diamine compound represented by formula (9) is normally from 0.5 equivalents to 1.2 equivalents and preferably from 0.8 equivalents to 1 equivalent.

In the reaction in which the acrylamide compound represented by formula (12) acts on the amine compound represented by formula (11), the amount of the amine compound represented by formula (11) that is caused to react relative to the acrylamide compound represented by formula (12) is normally from 0.8 equivalents to 2 equivalents and preferably from 1 equivalent to 1.5 equivalents.

In the reaction in which the acrylamide compound represented by formula (10) acts on the diamine compound represented by formula (9), an aromatic amine such as pyridine, N,N-dimethyl-4-aminopyridine, pyrazine, or 2,6-lutidine or an aliphatic amine such as trimethylamine, triethylamine, pyrrolidine, piperidine, or piperazine may be used as a base with respect to the diamine compound represented by formula (9). The amount of such bases that is caused to react relative to the diamine compound represented by formula (9) is normally from 0.5 equivalents to 1.2 equivalents and preferably from 0.8 equivalents to 1 equivalent.

In the reaction in which the acrylamide compound represented by formula (12) acts on the amine compound represented by formula (11), an aromatic amine such as pyridine, N,N-dimethyl-4-aminopyridine, pyrazine, or 2,6-lutidine or an aliphatic amine such as trimethylamine, triethylamine, pyrrolidine, piperidine, or piperazine may be used as a base with respect to the amine compound represented by formula (11). The amount of such bases that is caused to react relative to the amine compound represented by formula (11) is normally from 0.5 equivalents to 1.2 equivalents and preferably from 0.8 equivalents to 1 equivalent.

Note that in a situation in which the substituents $R^1$ and $R^2$ are the same, the diamide compound represented by formula (Ic) can be produced through a single-step reaction in which at least 2 equivalents of the acrylamide compound represented by formula (10) is used relative to the diamine compound represented by formula (9).

The reactions can normally be carried out in a temperature range of from −78° C. to the boiling temperature of the solvent that is used. However, the reactions are normally carried out at approximately −10° C. to 50° C. and preferably at around room temperature.

Although it is not possible to make generalizations about the reaction time since the reaction time varies depending on the reaction temperature and so forth, the reactions are normally completed in approximately 0.5 hours to 24 hours.

(Reaction formula 4)

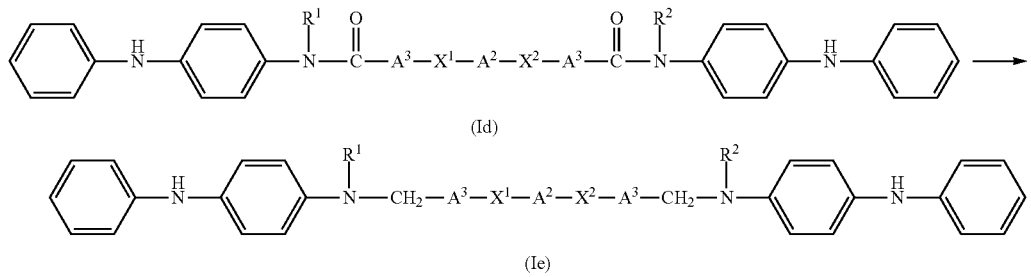

(In reaction formula 4, $R^1$, $R^2$, $A^2$, $X^1$, and $X^2$ are the same as previously described and $A^3$ represents an alkylene group having a carbon number of 1-6.)

According to reaction formula 4, a diamino compound represented by formula (Ie) can be produced by causing a reducing agent to act on a diamide compound represented by formula (Id) in a solvent in order to reduce amide carbonyl bonds. The diamide compound represented by formula (Id) and the diamino compound represented by formula (Ie) are compounds that are included within the scope of the presently disclosed bisanilino compound represented by formula (I). The diamide compound represented by formula (Id) can be produced according to the reactions in reaction formulae 1-3.

The solvent that is used in the reaction in reaction formula 4 can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, in the case of a borohydride reducing agent, alcohol solvents such as methanol, ethanol, n-propanol, isopropyl alcohol, and n-bu-tanol. One of these solvents may be used individually, or a mixture of two or more of these solvents may be used as necessary.

The amount of such solvents that is used relative to 1 part by mass of the diamide compound represented by formula (Id) is normally approximately 1 part by mass to 500 parts by mass and preferably approximately 5 parts by mass to 100 parts by mass.

Examples of reducing agents that can be used in reaction formula 4 include lithium aluminum hydride, sodium borohydride, borane, and diborane. Furthermore, lithium aluminum hydride may be used in combination with aluminum chloride, or sodium borohydride may be used in combination with a Lewis acid such as tin tetrachloride or boron trifluoride diethyl ether complex.

The amount of such reducing agents that is used relative to the diamide compound represented by formula (Id) is normally from 1.5 equivalents to 20.0 equivalents, preferably from 1.5 equivalents to 6.0 equivalents, and more preferably 1.5 equivalents.

The reaction in reaction formula 4 can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

(Reaction formula 5)

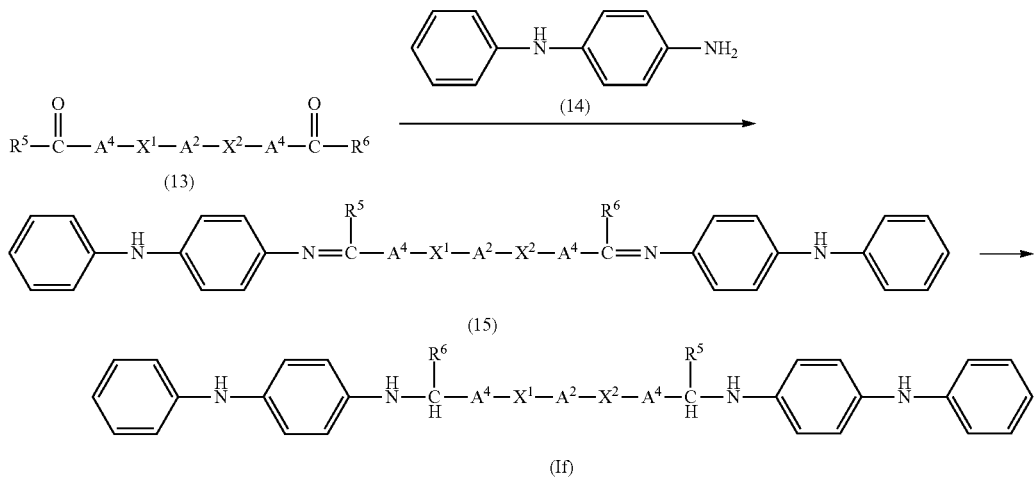

(In reaction formula 5, $A^2$, $X^1$, and $X^2$ are the same as previously described, $R^5$ and $R^6$ each represent a hydrogen atom or an alkyl group having a carbon number of 1-4, and $A^4$ represents an alkylene group having a carbon number of 1-6.)

According to reaction formula 5, a diamino compound represented by formula (If) can be produced by causing p-anilinoaniline represented by formula (14) to act on a dicarbonyl compound represented by formula (13) to produce a diimino compound represented by formula (15) and subsequently causing a reducing agent to act on the diimino compound represented by formula (15) or carrying out a catalytic hydrogen reduction reaction on the diimino compound represented by formula (15) in the presence of a metal catalyst.

Furthermore, the diamino compound represented by formula (If) can be directly produced by carrying out a reductive amination reaction in which at least 2 equivalents of the aniline compound represented by formula (14) is caused to act on the dicarbonyl compound represented by formula (13) in the presence of a reducing agent or through a catalytic hydrogen reduction reaction in the presence of a metal catalyst.

The diamino compound represented by formula (If) is a compound that is included within the scope of the presently disclosed bisanilino compound represented by formula (I).

The reaction in which p-anilinoaniline represented by formula (14) acts on the dicarbonyl compound represented by formula (13) to produce the diimino compound represented by formula (15) (first reaction) is preferably carried out in a solvent that can be selected from a wide range of commonly known solvents that are inert with respect to the reaction. Examples of solvents that can be used in the first reaction include ether solvents such as dimethyl ether, diethyl ether, diisopropyl ether, tert-butyl methyl ether, tetrahydrofuran, dioxane, tetrahydropyran, and 1,2-dimethoxyethane; organic solvents such as toluene, xylene, and benzene; halogen-containing solvents such as dichloromethane and carbon tetrachloride; alcohols such as methanol, ethanol, n-propanol, isopropyl alcohol, and n-butanol; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the dicarbonyl compound represented by formula (13) is normally approximately 1 part by mass to 500 parts by mass and preferably approximately 5 parts by mass to 100 parts by mass.

In the first reaction, the dicarbonyl compound represented by formula (13) and p-anilinoaniline represented by formula (14) are used in proportions such that the amount of p-anilinoaniline represented by formula (14) relative to the dicarbonyl compound represented by formula (13) is normally from 2 equivalents to 20 equivalents, preferably from 2 equivalents to 5 equivalents, and more preferably from 2 equivalents to 3 equivalents.

The first reaction can normally be carried out in a temperature range of from $-78°$ C. to the boiling temperature of the solvent that is used. However, the first reaction is normally carried out at approximately $-10°$ C. to $50°$ C. and preferably at around room temperature.

Although it is not possible to make generalizations about the reaction time since the reaction time varies depending on the reaction temperature and so forth, the first reaction is normally completed in approximately 0.5 hours to 24 hours.

The reaction in which the reducing agent acts on the diimino compound represented by formula (15) to produce the diamino compound represented by formula (If) (second reaction) is preferably carried out in a solvent that can be selected from a wide range of commonly known solvents that are inert with respect to the reaction. Examples of solvents that can be used in the second reaction include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, particularly in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the diimino compound represented by formula (15) is normally approximately 1 part by mass to 500 parts by mass and preferably approximately 5 parts by mass to 100 parts by mass.

Examples of reducing agents that can be used in the second reaction include lithium aluminum hydride, sodium borohydride, lithium borohydride, sodium cyanoborohydride, and lithium triethylborohydride.

The amount of such reducing agents that is used relative to the diimino compound represented by formula (15) is normally from 0.5 equivalents to 10 equivalents, preferably from 0.5 equivalents to 2.0 equivalents, and more preferably from 0.5 equivalents to 1.0 equivalents.

The second reaction can normally be carried out in a temperature range of from $-78°$ C. to the boiling temperature of the solvent that is used. However, the second reaction is normally carried out at approximately $-10°$ C. to $50°$ C. and preferably at around room temperature.

Although it is not possible to make generalizations about the reaction time since the reaction time varies depending on the reaction temperature and so forth, the second reaction is normally completed in approximately 0.5 hours to 24 hours.

The reaction in which a catalytic hydrogen reduction reaction of the diimino compound represented by formula (15) is carried out in the presence of a metal catalyst to produce the diamino compound represented by formula (If) (second reaction) is preferably carried out in a solvent that can be selected from a wide range of commonly known solvents that are inert with respect to the reaction. Examples of solvents that can be used in the second reaction include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the diimino compound represented by formula (15) is normally approximately 1 part by mass to 500 parts by mass and preferably approximately 1 part by mass to 20 parts by mass.

Examples of metal catalysts that can be used in the catalytic hydrogen reduction reaction in reaction formula 5 include palladium on carbon, platinum black (platinum on carbon), sulfided platinum on carbon, platinum oxide, Raney nickel, and Raney cobalt.

The amount of such metal catalysts that is used relative to the diimino compound represented by formula (15) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from $-78°$ C. to the boiling temperature of the solvent that is used. However, the reaction is normally carried out at approximately −10° C. to 50° C. and preferably at around room temperature.

The reaction is carried out under a hydrogen atmosphere at a pressure that is normally from atmospheric pressure to 10 MPa, preferably from atmospheric pressure to 1.0 MPa, and more preferably around atmospheric pressure.

Although it is not possible to make generalizations about the reaction time since the reaction time varies depending on the reaction temperature and so forth, the reaction is normally completed in approximately 0.5 hours to 24 hours.

The reductive amination reaction in which at least 2 equivalents of the aniline compound represented by formula (14) acts on the dicarbonyl compound represented by formula (13) in the presence of a reducing agent to directly produce the diamino compound represented by formula (If) is preferably carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, particularly in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the dicarbonyl compound represented by formula (13) is normally approximately 1 part by mass to 500 parts by mass and preferably approximately 5 parts by mass to 100 parts by mass.

Examples of reducing agents that can be used in the reaction include lithium aluminum hydride, sodium borohydride, lithium borohydride, sodium cyanoborohydride, and lithium triethylborohydride.

The amount of such reducing agents that is used relative to the dicarbonyl compound represented by formula (13) is normally from 0.5 equivalents to 10 equivalents, preferably from 0.5 equivalents to 2.0 equivalents.

The reaction can normally be carried out in a temperature range of from −78° C. to the boiling temperature of the solvent that is used. However, the second reaction is normally carried out at approximately −10° C. to 50° C. and preferably at around room temperature.

Although it is not possible to make generalizations about the reaction time since the reaction time varies depending on the reaction temperature and so forth, the second reaction is normally completed in approximately 0.5 hours to 24 hours.

The reductive amination reaction in which at least 2 equivalents of the aniline compound represented by formula (14) acts on the dicarbonyl compound represented by formula (13) through a catalytic hydrogen reduction reaction in the presence of a metal catalyst to directly produce the diamino compound represented by formula (If) is preferably carried out in a solvent that can be selected from a wide range of commonly known solvents that are inert with respect to the reaction. Examples of solvents that can be used include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the dicarbonyl compound represented by formula (13) is normally approximately 1 part by mass to 500 parts by mass and preferably approximately 1 part by mass to 20 parts by mass.

Examples of metal catalysts that can be used in the catalytic hydrogen reduction reaction include palladium on carbon, platinum black (platinum on carbon), sulfided platinum on carbon, platinum oxide, Raney nickel, and Raney cobalt.

The amount of such metal catalysts that is used relative to the dicarbonyl compound represented by formula (13) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from −78° C. to the boiling temperature of the solvent that is used. However, the reaction is normally carried out at approximately −10° C. to 50° C. and preferably at around room temperature.

The reaction is carried out under a hydrogen atmosphere at a pressure that is normally from atmospheric pressure to 10 MPa, preferably from atmospheric pressure to 1.0 MPa, and more preferably around atmospheric pressure.

Although it is not possible to make generalizations about the reaction time since the reaction time varies depending on the reaction temperature and so forth, the reaction is normally completed in approximately 0.5 hours to 24 hours.

In a situation in which the bisanilino compound represented by formula (I) is used as an anti-aging agent, the blending amount of the bisanilino compound relative to 100 parts by mass of the rubber component is preferably in a range of from 0.2 parts by mass to 10 parts by mass and more preferably in a range of from 0.5 parts by mass to 7.5 parts by mass. As a result of the blending amount of the bisanilino compound represented by formula (I) being at least 0.2 parts by mass relative to 100 parts by mass of the rubber component, weather resistance of the rubber composition, such as ozone resistance, can be sufficiently improved and surface discoloration of a rubber article can be effectively inhibited. On the other hand, it is advantageous in terms of raw material costs of the rubber composition for the blending amount of the bisanilino compound represented by formula (I) to be no greater than 10 parts by mass relative to 100 parts by mass of the rubber component since this enables the amount of the bisanilino compound represented by formula (I) that is consumed as the anti-aging agent to be restricted while sufficiently improving weather resistance and inhibiting discoloration.

It should be noted that the presently disclosed rubber composition may contain the bisanilino compound represented by formula (I) in combination with another anti-aging agent such as an amine-based anti-aging agent. In such a situation, the blending amount of the anti-aging agent other than the bisanilino compound represented by formula (I) is preferably in a range of from 0 parts by mass to 5 parts by mass relative to 100 parts by mass of the rubber component.

<<Other Components>>

The presently disclosed rubber composition may contain carbon black, silica, or the like as a reinforcing filler. No specific limitations are placed on the carbon black that is used. Likewise, the silica can be any commercially available silica, among which, wet silica, dry silica, and colloidal silica are preferable, and wet silica is more preferable. The blending amount of the reinforcing filler is preferably in a range of from 5 parts by mass to 200 parts by mass relative to 100 parts by mass of the rubber component. In a situation in which silica is used as a reinforcing filler, it is preferable that a silane coupling agent is contained in an amount of approximately 1 mass % to 20 mass % relative to the silica from a viewpoint of reinforcing properties and it is more preferable that the silane coupling agent is contained in a range of from 6 mass % to 12 mass % from a viewpoint of heat-generation properties.

The presently disclosed rubber composition may further contain compounding agents commonly used in the rubber industry that are appropriately selected so as not to impair the objectives of the present disclosure. Examples of such compounding agents include vulcanizing agents, vulcanization accelerators, anti-scorch agents, softeners, zinc oxide, and stearic acid. Commercially available products may be suitably used as the compounding agents. The rubber composition can be produced by kneading, warming, extrusion, and the like of the rubber component, the bisanilino compound represented by formula (I), and various compounding agents that are appropriately selected as necessary.

propyl ether and dried under reduced pressure to yield 21.9 g (85% yield) of N-(4-anilinophenyl)acrylamide as a gray solid.

(2) Production of N,N'-bis(4-anilinophenyl)-3,3'-(hexan-1,6-diyldiimino)dipropaneamide (Compound I-1)

After 21.9 g of N-(4-anilinophenyl)acrylamide had been added to a solution of 5.34 g of hexamethylenediamine in 100 mL of methanol at room temperature, the solution was stirred for 1 week at room temperature. The resultant reaction liquid was concentrated to obtain a residue that was then crystallized through addition of a mixed liquid of diisopropyl ether and isopropyl alcohol. The crystals were filtered off, washed with isopropyl alcohol, and dried under reduced pressure to yield 12.4 g (45% yield) of N,N'-bis(4-anilinophenyl)-3,3'-(hexan-1,6-diyldiimino)dipropaneamide (compound I-1) represented by the following formula.

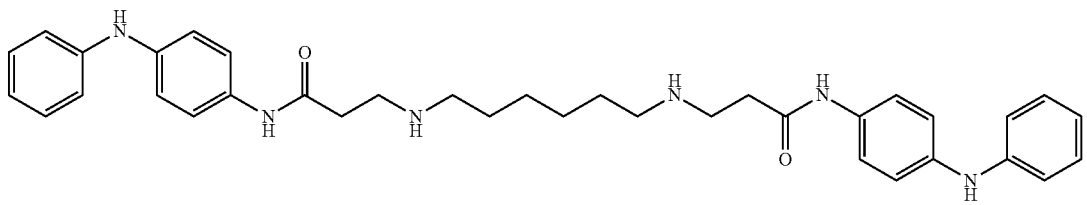

(I-1)

<Tire>

A presently disclosed tire includes at least one tire member in which the above-described rubber composition is used. A tread and a sidewall that are exposed at the outer surface are preferable examples of the aforementioned tire member. Through use of the above-described rubber composition, the presently disclosed tire benefits from superior weather resistance and inhibition of rubber article surface discoloration.

EXAMPLES

The following provides a more detailed explanation of the present disclosure through examples and production examples. However, the present disclosure is not in any way limited by the following examples.

Production Example 1: Production of N,N'-bis(4-anilinophenyl)-3,3'-(hexan-1,6-diyldiimino)dipropaneamide (Compound I-1)

(1) Production of N-(4-anilinophenyl)acrylamide

A solution of 40.0 g of N-phenyl-p-phenylenediamine in 300 mL of dehydrated tetrahydrofuran was ice cooled and, after a solution of 9.84 g of acryloyl chloride in 20 mL of dehydrated tetrahydrofuran had been dripped therein, was returned to room temperature and was stirred overnight. The resultant reaction liquid was poured into water and was extracted with ethyl acetate. The organic layer was washed with 1N hydrochloric acid, saturated sodium hydrogen carbonate aqueous solution, and saturated saline in this order, was dried using anhydrous magnesium sulfate, and was subsequently concentrated under reduced pressure to obtain a solid residue. The solid residue was washed with diiso- Properties: Gray solid Melting point: 138-140° C.

$^1$H-NMR (300 MHz, DMSO-D$_6$, δ ppm): 1.30 (m, 8H), 1.70 (br-s, 2H), 2.38 (m, 4H), 2.76 (m, 4H), 6.74 (m, 2H), 6.98 (m, 8H), 7.17 (m, 4H), 7.43 (m, 4H), 7.97 (s, 2H), 9.96 (s, 2H)

Methylene 4H was detected overlapping with the signal of DMSO at 2.49 ppm.

Production Example 2: Production of N,N'-bis(4-anilinophenyl)-2,2'-[hexan-1,6-diylbis(sulfandiyl)]bisacetamide (Compound I-2)

(1) Production of N-(4-anilinophenyl)chloroacetamide

A solution of 100 g of N-phenyl-p-phenylenediamine in 500 mL of dehydrated tetrahydrofuran was ice cooled and, after a solution of 30.7 g of chloroacetyl chloride in 100 mL of dehydrated tetrahydrofuran had been dripped therein, was returned to room temperature and was stirred overnight. The resultant reaction liquid was poured into water and was extracted with ethyl acetate. The organic layer was washed with 1N hydrochloric acid, saturated sodium hydrogen carbonate aqueous solution, and saturated saline in this order, was dried using anhydrous magnesium sulfate, and was subsequently concentrated under reduced pressure to obtain a solid residue. The solid residue was washed with diisopropyl ether and dried under reduced pressure to yield 57.5 g (81% yield) of N-(4-anilinophenyl)chloroacetamide as a gray solid.

(2) Production of N,N'-bis(4-anilinophenyl)-2,2'-[hexan-1,6-diylbis(sulfandiyl)]bisacetamide (Compound I-2)

A suspension of 35.0 g of N-(4-anilinophenyl)chloroacetamide and 55.5 g of potassium carbonate in 350 mL of acetonitrile was prepared, was ice cooled while 10.1 g of 1,6-hexanedithiol was dripped therein, and was then returned to room temperature and stirred for 2 days. The resultant reaction liquid was filtered to obtain a solid that was then washed with acetonitrile and subsequently crushed and washed with water. The resultant solid was washed with acetonitrile and dried under reduced pressure to yield 37.9 g (95% yield) of N,N'-bis(4-anilinophenyl)-2,2'-[hexan-1,6-diylbis(sulfandiyl)]bisacetamide (compound I-2) represented by the following formula.

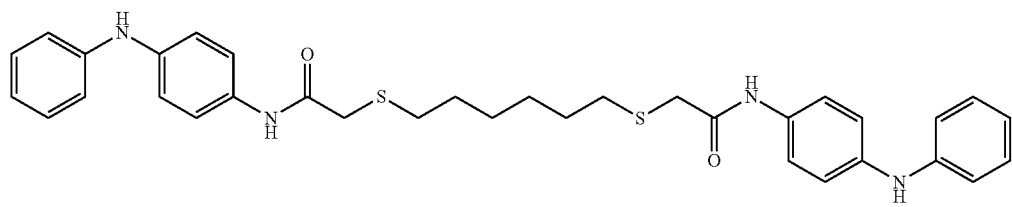

(I-2)

Properties: Pale purple solid

Melting point: 154-156° C.

$^1$H-NMR (300 MHz, DMSO-D$_6$, δ ppm): 1.33 (m, 4H), 1.54 (m, 4H), 2.60 (t, 4H), 3.23 (s, 4H), 6.75 (m, 2H), 7.00 (m, 8H), 7.18 (m, 4H), 7.43 (m, 4H), 8.02 (s, 2H), 9.87 (s, 2H)

Production Example 3: Production of N,N'-bis(4-anilinophenyl)-N,N'-diisopropyl-2,2'-[hexan-1,6-diylbis(sulfandiyl)]bisacetamide (Compound I-3)

(1) Production of N-(4-anilinophenyl)-N'-(isopropyl)chloroacetamide

A solution of 100.0 g of N-isopropyl-N'-phenyl-p-phenylenediamine in 450 mL of dehydrated tetrahydrofuran was ice cooled and, after a solution of 25.0 g of chloroacetyl chloride in 50 mL of dehydrated tetrahydrofuran had been dripped therein, was returned to room temperature and stirred for 1 week. The resultant reaction liquid was poured into water, precipitated solid was removed by filtration, and the filtrate was extracted with ethyl acetate. The organic layer was washed with 1N hydrochloric acid, saturated sodium hydrogen carbonate aqueous solution, and saturated saline in this order, was dried using anhydrous magnesium sulfate, and was subsequently concentrated under reduced pressure. Solid that had precipitated in the concentrated liquid was filtered off, washed with diisopropyl ether, and dried under reduced pressure to yield 61.9 g (93% yield) of N-(4-anilinophenyl)-N'-(isopropyl)chloroacetamide as a gray solid.

(2) Production of N,N'-bis(4-anilinophenyl)-N,N'-diisopropyl-2,2'-[hexan-1,6-diylbis(sulfandiyl)]bisacetamide (Compound I-3)

A suspension of 1.20 g of N-(4-anilinophenyl)-N'-(isopropyl)chloroacetamide and 1.64 g of potassium carbonate in 40 mL of acetonitrile was prepared and, after 300 mg of 1,6-hexanedithiol had been added thereto at room temperature, was stirred for 4 days. The resultant reaction liquid was filtered to obtain a solid. The solid was washed with acetonitrile, was subsequently crushed and washed with water and acetonitrile in this order, and was then dried under reduced pressure to yield 1.15 g (85% yield) of N,N'-bis(4-anilinophenyl)-N,N'-diisopropyl-2,2'-[hexan-1,6-diylbis(sulfandiyl)]bisacetamide (compound I-3) represented by the following formula.

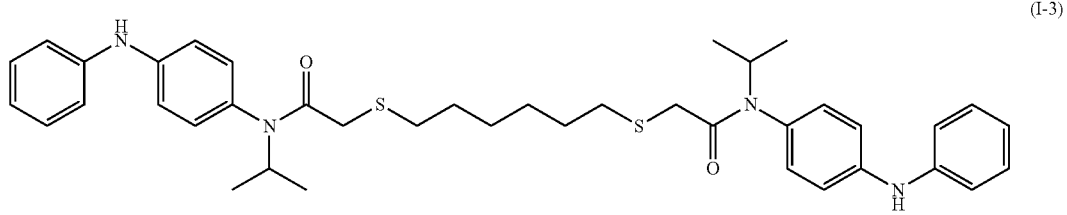 [SMILES: CC(C)N(C(=O)CSCCCCCCSCC(=O)N(c1ccc(Nc2ccccc2)cc1)C(C)C)c1ccc(Nc2ccccc2)cc1]

(I-3)

Properties: Gray solid

Melting point: 143-145° C.

$^1$H-NMR (300 MHz, DMSO-D$_6$, δ ppm): 0.96 (d, 12H), 1.22 (m, 4H), 1.36 (m, 4H), 2.42 (t, 4H), 2.89 (s, 4H), 4.73 (m, 2H), 6.86 (m, 2H), 7.06 (m, 12H), 7.25 (m, 4H), 8.34 (s, 2H)

Production Example 4: Production of N,N'-bis[2-(4-anilinoanilino)ethyl]-N,N'-dimethylethane-1,2-diamine (Compound I-4)

(1) Production of N-(4-anilinophenyl)chloroacetamide

A solution of 228 g of N-phenyl-p-phenylenediamine in 1,400 mL of tetrahydrofuran was ice cooled and, after 70.0 g of chloroacetyl chloride had been dripped therein, was stirred for 1 hour at room temperature. Water and ethyl acetate were added to the resultant reaction liquid and liquid separation was performed to obtain an organic layer. The organic layer was washed with 500 mL of 1N hydrochloric acid, was dried using anhydrous magnesium sulfate, and was subsequently concentrated under reduced pressure to obtain a solid residue. The solid residue was washed with diisopropyl ether and ethyl acetate in this order, and was dried under reduced pressure to yield 151 g (93% yield) of N-(4-anilinophenyl)chloroacetamide as a white solid.

(2) Production of N,N'-bis(4-anilinophenyl)-2,2'-[ethylenebis(methylimino)]bisacetamide After 100 mL of acetonitrile, 4.6 g of potassium carbonate, and 1.16 g of N,N'-dimethylethylenediamine had been added to 6.9 g of N-(4-anilinophenyl)chloroacetamide, stirring was performed overnight while heating under reflux. The resultant reaction liquid was cooled to room temperature and, after water and ethyl acetate had been added thereto, liquid separation was performed to obtain an organic layer. The organic layer was dried using anhydrous magnesium sulfate and was subsequently concentrated under reduced pressure to obtain a solid residue. The solid residue was washed with a mixed liquid of hexane/ethyl acetate (1:1) and dried under reduced pressure to yield 6.8 g (96% yield) of N,N'-bis(4-anilinophenyl)-2,2'-[ethylenebis(methylimino)]bisacetamide as a white solid.

(3) Production of N,N'-bis[2-(4-anilinoanilino)ethyl]-N,N'-dimethylethane-1,2-diamine (Compound I-4)

A suspension of 12.6 g of lithium aluminum hydride in 600 mL of dehydrated tetrahydrofuran was prepared and, after 27.4 g of N,N'-bis(4-anilinophenyl)-2,2'-[ethylenebis(methylimino)]bisacetamide, produced according to the description in section (2), had been added thereto under ice cooling, the suspension was returned to room temperature and stirred for 1 hour, and was subsequently heated under reflux overnight. The resultant reaction liquid was ice cooled and was quenched with 200 mL of water. Thereafter, 100 mL of 1N sodium hydroxide aqueous solution and 100 mL of water were added and stirring was performed to produce a slurry that was subsequently filtered using Celite. The filtrate was concentrated under reduced pressure to obtain a residue that was then washed with a mixed liquid of hexane/ethyl acetate (1:1) to yield 16.1 g (62% yield) of N,N'-bis[2-(4-anilinoanilino)ethyl]-N,N'-dimethylethane-1,2-diamine (compound I-4) represented by the following formula.

Production Example 5: Production of N,N'-bis{2-[(4-anilinophenyl)(isopropyl)amino]ethyl}-N,N'-dimethylethane-1,2-diamine (Compound I-5)

(1) Production of N-(4-anilinophenyl)-N-isopropylchloroacetamide

After 10.7 g of triethylamine had been added to a solution of 22.0 g of N-isopropyl-N'-phenyl-p-phenylenediamine in 100 mL of toluene, the solution was ice cooled and 10.0 g of chloroacetyl chloride was dripped therein. Stirring was then performed for 1 hour at room temperature and the resultant reaction liquid was filtered after 200 mL of water had been added thereto. Filtered off solid was washed with water and toluene in this order, and was subsequently dried under reduced pressure to yield 23.9 g (89% yield) of N-(4-anilinophenyl)-N-isopropylchloroacetamide as a gray-white solid.

(2) Production of N,N'-bis(4-anilinophenyl)-N,N'-diisopropyl-2,2'-[ethylenebis(methylimino)]bisacetamide After 500 mL of acetonitrile, 47.0 g of potassium carbonate, and 10.0 g of N,N'-dimethylethylenediamine had been added to 69.2 g of N-(4-anilinophenyl)-N-isopropylchloroacetamide, produced according to the description in section (1), heating under reflux was performed overnight. The resultant reaction liquid was cooled to room temperature and, after 1,000 mL of water had been added thereto, was filtered to obtain a solid. The solid was washed with water and ethyl acetate in this order, and was dried under reduced pressure to yield 66.6 g (95% yield) of N,N'-bis(4-anilinophenyl)-N,N'-diisopropyl-2,2'-[ethylenebis(methylimino)]bisacetamide as a white solid.

(3) Production of N,N'-bis{2-[(4-anilinophenyl)(isopropyl)amino]ethyl}N,N'-dimethylethane-1,2-diamine (Compound I-5)

A suspension of 7.6 g of lithium aluminum hydride in 400 mL of dehydrated tetrahydrofuran was prepared and, after 16.5 g of N,N'-bis(4-anilinophenyl)-N,N'-diisopropyl-2,2'-[ethylenebis(methylimino)]bisacetamide had been added thereto under ice cooling, the suspension was returned to room temperature and stirred for 1 hour, and was subsequently heated under reflux overnight. The resultant reaction liquid was ice cooled and was quenched with 100 mL of water. Thereafter, 50 mL of 1N sodium hydroxide aqueous (I-4)

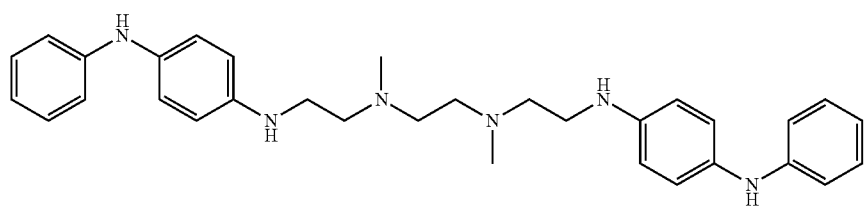

Properties: White solid
Melting point: 121° C.
$^1$H-NMR (300 MHz, DMSO-D$_6$, δ ppm): 2.22 (s, 6H), 2.48 (m, 4H), 2.54 (t, 4H), 3.05 (dt, 4H), 5.10 (m, 2H), 6.56 (m, 6H), 6.76 (d, 4H), 6.87 (d, 4H), 7.06 (dd, 4H), 7.47 (s, 2H)

solution and 100 mL of water were added and stirring was performed to produce a slurry that was subsequently filtered using Celite. The filtrate was concentrated under reduced pressure to obtain a residue that was then dissolved in chloroform and purified by silica gel column chromatography (ethyl acetate:methanol=1:1→3:2) to yield 8.6 g (54% yield) of N,N'-bis{2-[(4-anilinophenyl)(isopropyl)amino]ethyl}-N,N'-dimethylethane-1,2-diamine (compound I-5) represented by the following formula.

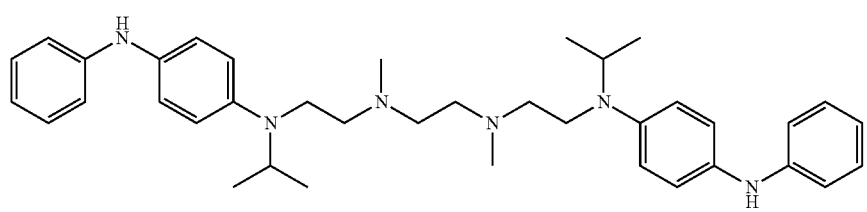

(I-5)

Properties: White solid
Melting point: 121° C.
$^1$H-NMR (300 MHz, CDCl$_3$, δ ppm): 1.16 (d, 12H), 2.33 (s, 6H), 2.53 (m, 8H), 3.26 (t, 4H), 3.93 (m, 2H), 5.38 (s, 2H), 6.78 (m, 6H), 6.84 (d, 4H), 7.04 (d, 4H), 7.17 (dd, 4H)

Production Example 6: Production of N',N'''-diphenyl-N,N''-[hexan-1,6-diylbis(oxyethylene)]dibenzene-1,4-diamine (Compound I-6)

(1) Production of 2,2'-(hexan-1,6-diyldioxy)diacetic acid

A solution of 10 g of 1,6-hexanediol in 150 mL of dehydrated tetrahydrofuran was ice cooled and, after 14.2 g of sodium hydride (60% oil suspension) had been added thereto, was returned to room temperature and stirred for 1 hour. The solution was once again ice cooled and 16.8 g of chloroacetic acid was added thereto. After the resultant solution had been returned to room temperature and stirred overnight, 50 mL of N,N-dimethylformamide was added thereto and heating under reflux was performed overnight. The resultant reaction liquid was left to cool, was poured into water, and, after 3N hydrochloric acid had been added thereto, was extracted with ethyl acetate. The resultant organic layer was dried using anhydrous magnesium sulfate and concentrated under reduced pressure to yield 31.0 g of a crude product of 2,2'-(hexan-1,6-diyldioxy)diacetic acid as a yellow oil.

(2) Production of N,N'-bis(4-anilinophenyl)-2,2'-(hexan-1,6-diyloxy)bisacetamide A solution of 31.0 g of the crude product of 2,2'-(hexan-1,6-diyldioxy)diacetic acid dissolved in 60 mL of chloroform was prepared and, after 50.0 g of thionyl chloride had been added thereto, was heated under reflux for 5 hours. Next, chloroform and excess thionyl chloride were distilled by heating under atmospheric pressure to obtain a residue. A solution was prepared by adding 50 mL of dehydrated tetrahydrofuran to the residue and was dripped into a solution of 38.8 g of N-phenyl-p-phenylenediamine in 500 mL of dehydrated tetrahydrofuran and 18.2 g of pyridine under ice cooling. After stirring had been performed overnight at room temperature, the resultant reaction liquid was poured into water and was extracted with ethyl acetate. The resultant organic layer was washed with 1N hydrochloric acid, saturated sodium hydrogen carbonate aqueous solution, and saturated saline in this order, was dried using anhydrous magnesium sulfate, and was subsequently concentrated under reduced pressure. The resultant crude product was purified by silica gel column chromatography (hexane:ethyl acetate=1:1→1:3) to obtain a solid that was then washed with a mixed liquid of hexane, ethyl acetate, and diisopropyl ether and dried under reduced pressure to yield 27.2 g (57% yield) of N,N'-bis(4-anilinophenyl)-2,2'-(hexan-1,6-diyloxy)bisacetamide as a brown solid.

(3) Production of N',N'''-diphenyl-N,N''-[hexan-1,6-diylbis(oxyethylene)]dibenzene-1,4-diamine (Compound I-6)

A suspension of 10.6 g of lithium aluminum hydride in 500 mL of dehydrated tetrahydrofuran was prepared and 26.4 g of N,N'-bis(4-anilinophenyl)-2,2'-(hexan-1,6-diyloxy)bisacetamide was gradually added thereto under ice cooling. Stirring was performed for 1 hour at room temperature and heating under reflux was subsequently performed overnight. The resultant reaction liquid was ice cooled and was quenched with 20.2 mL of water. Thereafter, 20 mL of 1N sodium hydroxide aqueous solution and 20 mL of water were added and stirring was performed to produce a slurry that was subsequently filtered using Celite. The filtrate was concentrated under reduced pressure and the resultant residue was purified by silica gel column chromatography (hexane:ethyl acetate=1:1) to obtain a solid. The solid was washed with a mixed liquid of hexane and ethyl acetate to yield 21.9 g (87% yield) of N',N'''-diphenyl-N,N''-[hexan-1,6-diylbis(oxyethylene)]dibenzene-1,4-diamine (compound I-6) represented by the following formula.

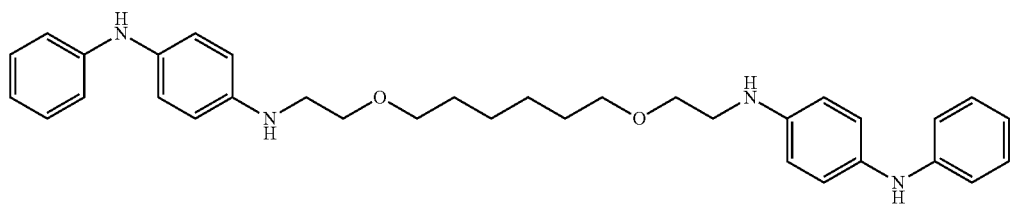

(I-6)

Properties: Beige solid

Melting point: 82° C.

$^1$H-NMR (300 MHz, DMSO-D$_6$, δ ppm): 1.32 (m, 4H), 1.51 (m, 4H), 3.14 (m, 4H), 3.40 (br-t, 4H), 3.51 (br-t, 4H), 5.20 (br-t, 2H), 6.58 (m, 6H), 6.78 (m, 4H), 6.88 (m, 4H), 7.08 (m, 4H), 7.50 (s, 2H)

Production Example 7: Production of N,N'''-diisopropyl-N',N'''-diphenyl-N,N''-[hexan-1,6-diylbis(oxyethylene)]dibenzene-1,4-diamine (Compound I-7)

(1) Production of N,N'-bis(4-anilinophenyl)-N,N'-diisopropyl-2,2'-(hexan-1,6-diyldioxy)bisacetamide A solution of 2.93 g of 1,6-hexanediol in 150 mL of dehydrated tetrahydrofuran was ice cooled and, after 2.18 g of sodium hydride (60% oil suspension) had been added thereto, was returned to room temperature and stirred for 1 hour. Thereafter, 15.0 g of N-(4-anilinophenyl)-N'-(isopropyl)chloroacetamide was added under ice cooling and stirring was performed for 3 days at room temperature. Ethyl acetate and water were added to the resultant reaction liquid and liquid separation was performed to obtain an organic layer. The organic layer was washed with water and saturated saline, was dried using anhydrous magnesium sulfate, and was subsequently concentrated under reduced pressure. The resultant solid residue was washed with a mixed liquid of diisopropyl ether and ethyl acetate and dried under reduced pressure to yield 14.0 g (87% yield) of N,N'-bis(4-anilinophenyl)-N,N'-diisopropyl-2,2'-(hexan-1,6-diyldioxy)bisacetamide as a gray solid.

(2) Production of N,N'''-diisopropyl-N',N'''-diphenyl-N,N''-[hexan-1,6-diylbis(oxyethylene)]dibenzene-1,4-diamine (Compound I-7)

A suspension of 5.57 g of lithium aluminum hydride in 200 mL of dehydrated tetrahydrofuran was prepared and was ice cooled while 14.0 g of N,N'-bis(4-anilinophenyl)-N,N'-diisopropyl-2,2'-(hexan-1,6-diyldioxy)bisacetamide was gradually added thereto. The suspension was then returned to room temperature and stirred for 1 hour, and was subsequently heated under reflux overnight. The resultant reaction liquid was ice cooled and was quenched with 10.9 mL of water. Thereafter, 32.6 mL of 1N sodium hydroxide aqueous solution and 22 mL of water were added and stirring was performed to produce a slurry that was subsequently filtered using Celite. The filtrate was concentrated under reduced pressure and the resultant residue was purified by silica gel column chromatography (hexane:ethyl acetate=2:1) to obtain a solid. The solid was washed with a mixed liquid of hexane and diisopropyl ether to yield 8.58 g (64% yield) of N,N'''-diisopropyl-N',N'''-diphenyl-N,N''-[hexan-1,6-diylbis(oxyethylene)]dibenzene-1,4-diamine (compound I-7) represented by the following formula.

Production Example 8: Production of N',N'''-diphenyl-N,N''-[ethylenebis(oxypentan-5,2-diyl)]dibenzene-1,4-diamine (Compound I-8)

(1) Production of 5,5'-ethylenedioxydipentan-2-one

After 350 mL of acetone and 149.9 g of sodium iodide had been added to 74.8 g of 1,2-bis(2-chloroethoxy)ethane, heating was performed under reflux for 48 hours. The resultant reaction liquid was filtered to remove inorganic salt and the filtrate was concentrated under reduced pressure. After 100 mL of dioxane had been added to the resultant residue, inorganic salt that had precipitated was once again removed by filtration and the filtrate was concentrated under reduced pressure to obtain a dioxane solution of 1,2-bis(2-iodoethoxy)ethane. Next, 100 mL of dioxane and 93.0 g of methyl acetoacetate were added to 95.6 g (0.20 mol) of the dioxane solution of 1,2-bis(2-iodoethoxy)ethane. Heating was then performed to 80° C. and, after 110.5 g of potassium carbonate had been gradually added, stirring was performed for 24 hours at from 80° C. to 85° C. The resultant reaction liquid was filtered and the filtrate was concentrated under reduced pressure to obtain a residue. Next, 160 g of 25% sodium hydroxide aqueous solution and 100 mL of water were added to the residue and stirring thereof was performed for 6 hours at 75° C. The resultant reaction liquid was cooled to room temperature and the top layer of two layers that had formed was extracted with dichloromethane. A solution was prepared by combining the extraction liquid and the lower layer in 100 mL of dichloromethane, was dried using anhydrous magnesium sulfate, and was subsequently concentrated under reduced pressure to yield 21.2 g (46% yield) of 5,5'-ethylenedioxydipentan-2-one.

(2) Production of N',N'''-diphenyl-N,N''-[ethylenebis(oxypentan-5,2-diyl)]dibenzene-1,4-diamine (Compound I-8)

After 200 mL of methanol, 20.2 g of N-phenyl-p-phenylenediamine, and 6.9 g of sodium cyanoborohydride had been added to 11.5 g of 5,5'-ethylenedioxydipentan-2-one, the pH was adjusted to 6.5-7.5 using acetic acid and stirring was performed for 33 hours at room temperature. Once elimination of 5,5'-ethylenedioxydipentan-2-one had been confirmed by $^1$H-NMR, 150 mL of dichloromethane and 300 mL of saturated sodium hydrogen carbonate aqueous solution were added. Liquid separation was performed to obtain (I-7)

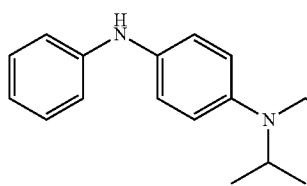 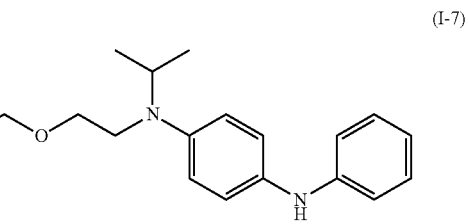

Properties: Green solid

Melting point: 52-53° C.

$^1$H-NMR (300 MHz, DMSO-$D_6$, δ ppm): 1.09 (d, 12H), 1.31 (m, 4H), 1.48 (m, 4H), 3.23 (m, 4H), 3.41 (m, 8H), 3.88 (m, 2H), 6.63 (m, 2H), 6.73 (m, 4H), 6.84 (m, 4H), 6.95 (m, 4H), 7.11 (m, 4H), 7.61 (s, 2H)

an organic layer that was then washed with 200 mL of saturated sodium hydrogen carbonate aqueous solution, dried using anhydrous magnesium sulfate, and subsequently concentrated under reduced pressure. Since separation of excess N-phenyl-p-phenylenediamine by silica gel column chromatography is difficult, 200 mL of methanol, 5.0 g of methyl isobutyl ketone, and 2.3 g of sodium cyanoborohydride were added to the concentrated residue and, after the pH had been adjusted to 6.5-7.5 using acetic acid, stirring was performed for 18 hours at room temperature. Thereafter, 200 mL of dichloromethane and 200 mL of saturated sodium hydrogen carbonate aqueous solution were added and liquid separation was performed to obtain an organic layer. The organic layer was dried using anhydrous magnesium sulfate and was subsequently concentrated under reduced pressure. The resultant residue was purified by silica gel column chromatography (hexane:ethyl acetate=5:1→3:1) to yield 16.3 g (58% yield) of N',N'''-diphenyl-N,N''-[ethylenebis(oxypentan-5,2-diyl)]dibenzene-1,4-diamine (compound I-8) represented by the following formula.

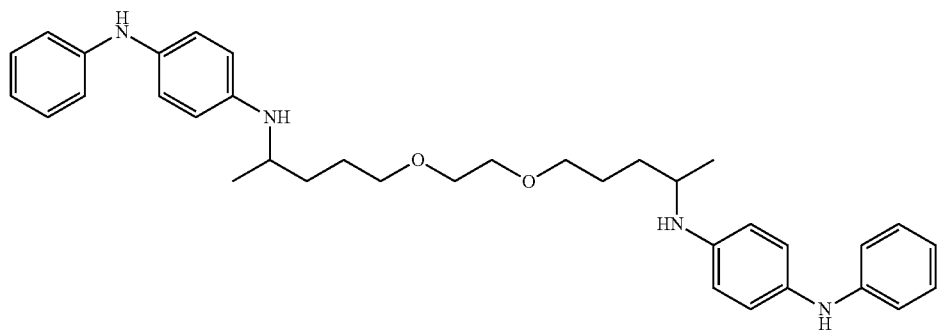

(I-8)

Properties: Black oil
$^1$H-NMR (300 MHz, DMSO-D$_6$, δ ppm): 1.08 (br-d, 6H), 1.40 (m, 2H), 1.53 (m, 6H), 3.36 (m, 6H), 3.47 (s, 4H), 5.01 (br-s, 2H), 6.53 (m, 4H), 6.59 (m, 2H), 6.77 (m, 4H), 6.86 (m, 4H), 7.08 (m, 4H), 7.45 (br-s, 2H)

Compounds I-9 to I-15 shown below in Table 1 were each produced in accordance with a method described in one the above production examples. The Physico-chemical properties of these compounds are shown in Table 2.

TABLE 1

| Compound number | Compound |
|---|---|
| I-9 | |
| I-10 | |
| I-11 | |

TABLE 1-continued

| Compound number | Compound |
|---|---|
| I-12 | |
| I-13 | |
| I-14 | |
| I-15 | |

TABLE 2

| Number | Properties | ¹H-NMR data |
|---|---|---|
| I-9 | Gray solid<br>Melting point<br>145-146° C. | $^1$H-NMR (300 MHz, DMSO-D$_6$, δ ppm): 0.95 (d, 12H), 1.40 (m, 4H), 3.27 (m, 4H), 3.58 (s, 4H), 4.74 (m, 2H), 6.87 (m, 2H), 7.04 (m, 12H), 7.25 (m, 4H), 8.33 (br-s, 2H) |
| I-10 | Gray solid<br>Melting point<br>162-164° C. | $^1$H-NMR (300 MHz, DMSO-D$_6$, δ ppm): 1.65 (m, 4H), 2.63 (m, 4H), 3.24 (s, 4H), 6.75 (m, 2H), 7.00 (m, 8H), 7.18 (m, 4H), 7.43 (m, 4H), 8.02 (br-s, 2H), 9.87 (br-s, 2H) |
| I-11 | Pale purple solid<br>Melting point<br>143-145° C. | $^1$H-NMR (300 MHz, DMSO-D$_6$, δ ppm): 0.95 (d, 12H), 1.43 (m, 4H), 2.44 (m, 4H), 2.89 (s, 4H), 4.73 (m, 2H), 6.86 (m, 2H), 7.05 (m, 12H), 7.25 (m, 4H), 8.34 (br-s, 2H) |
| I-12 | Gray-white solid<br>Melting point 142° C. | $^1$H-NMR (300 MHz, CDCl$_3$, δ ppm): 1.17 (d, 12H), 2.57 (m, 12H), 3.30 (m, 4H), 3.93 (m, 2H), 5.41 (s, 2H), 6.77 (m, 6H), 6.87 (d, 4H), 7.04 (d, 4H), 7.19 (dd, 4H) |
| I-13 | Brown oil | $^1$H-NMR (300 MHz, DMSO-D$_6$, δ ppm): 0.89 (d, 3H), 1.97 (m, 1H), 3.15 (m, 4H), 3.27 (m, 2H), 3.39 (m, 2H), 3.52 (t, 4H), 5.18 (br-t, 2H), 6.59 (m, 6H), 6.77 (m, 4H), 6.88 (m, 4H), 7.08 (m, 4H), 7.49 (s, 2H) |
| I-14 | Dark red-brown oil | $^1$H-NMR (300 MHz, DMSO-D$_6$, δ ppm): 0.86 (s, 6H), 3.15 (m, 8H), 3.52 (br-t, 4H), 5.11 (br-t, 2H), 6.59 (m, 6H), 6.78 (m, 4H), 6.87 (m, 4H), 7.08 (m, 4H), 7.49 (s, 2H) |
| I-15 | White solid<br>Melting point<br>91-92° C. | $^1$H-NMR (300 MHz, DMSO-D$_6$, δ ppm): 1.09 (d, 12H), 1.55 (m, 4H), 3.24 (br-t, 4H), 3.42 (m, 8H), 3.88 (m, 2H), 6.63 (m, 2H), 6.73 (m, 4H), 6.84 (m, 4H), 6.95 (m, 4H), 7.10 (m, 4H), 7.61 (s, 2H) |

Rubber compositions were produced by a standard method according to formulations 1 and 2 shown in Table 3. However, note that the blending amounts of various bisanilino compounds and anti-aging agents were changed depending on the example (refer to Tables 4 and 5 described further below). Formulation 1 is a formulation for a rubber composition that it is envisaged will be used in a tire tread and formulation 2 is a formulation for a rubber composition that it is envisaged will be used in a tire sidewall. Each of the produced rubber compositions was vulcanized by a standard method. Ozone resistance and discoloration of the resultant vulcanized rubber compositions were evaluated by the methods described further below.

TABLE 3

| Type of component | Formulations | |
| --- | --- | --- |
| | Formulation 1 Parts by mass | Formulation 2 Parts by mass |
| SBR *1 | 100 | — |
| BR | — | 50 |
| Natural rubber | — | 50 |
| Carbon black A *2 | 25 | — |
| Carbon black B *3 | — | 50 |
| Silica *4 | 25 | — |
| Silane coupling agent *5 | 2 | — |
| Stearic acid | 2 | 2 |
| Wax *6 | 2 | 2 |
| Zinc oxide | 3 | 3 |
| Vulcanization accelerator DPG *7 | 1.0 | 0.3 |
| Vulcanization accelerator MBTS *8 | 1.0 | 0.3 |
| Vulcanization accelerator CBS *9 | 1.0 | 0.8 |
| Sulfur | 1.5 | 2.0 |
| Bisanilino compound X *10 | Variable amount (refer to Tables 4 and 5) | |
| Bisanilino compound Y *11 | Variable amount (refer to Tables 4 and 5) | |
| Bisanilino compound Z *12 | Variable amount (refer to Tables 4 and 5) | |
| Anti-aging agent 6PPD *13 | Variable amount (refer to Tables 4 and 5) | |
| Anti-aging agent TMQ *14 | Variable amount (refer to Tables 4 and 5) | |

*1 SBR: Styrene-butadiene copolymer rubber, #1500 produced by JSR Corporation
*2 Carbon black A: SEAST 7HM produced by Tokai Carbon Co., Ltd.
*3 Carbon black B: SEAST F produced by Tokai Carbon Co., Ltd.
*4 Silica: Nipsil VN3 produced by Tosoh Silica Corporation
*5 Silane coupling agent: Bis(3-ethoxysilylpropyl)tetrasulfide
*6 Wax: Macrocrystalline wax, Ozoace 0701 produced by Nippon Seiro Co., Ltd.
*7 Vulcanization accelerator DPG: NOCCELER D produced by Ouchi Shinko Chemical Industrial Co., Ltd.
*8 Vulcanization accelerator MBTS: NOCCELER DM produced by Ouchi Shinko Chemical Industrial Co., Ltd.
*9 Vulcanization accelerator CBS: SANCELER CM-G produced by Sanshin Chemical Industry Co., Ltd.
*10 Bisanilino compound X: Compound I-7 produced in Production Example 7
*11 Bisanilino compound Y: Compound I-1 produced in Production Example 1
*12 Bisanilino compound Z: Compound I-8 produced in Production Example 8
*13 Anti-aging agent 6PPD: NOCRAC 6C produced by Ouchi Shinko Chemical Industrial Co., Ltd., N-phenyl-N'-(1,3-dimethylbutyl)-p-phenylenediamine
*14 Anti-aging agent TMQ: NONFLEX RD-S produced by Seiko-Chemical Co., Ltd., polymerized 2,2,4-trimethyl-1,2-dihydroquinoline <Ozone Resistance>

A test piece of each of the rubber compositions was subjected to an ozone degradation test in accordance with JIS K6301 under conditions of a temperature of 40° C., an ozone concentration of 50 pphm, and elongation of 20%. After 50 hours had passed, the state of degradation of the test piece was inspected and was evaluated using the following three-level scale based on the number of cracks that had formed.

A: Small number of cracks
B: Large number of cracks
C: Countless number of cracks Moreover, the test piece was evaluated using the following five-level scale based on the size and depth of cracks.

1: Cracks not visible by naked eye but visible under ×10 magnifying glass
2: Cracks visible by naked eye
3: Deep and relatively large cracks (less than 1 mm)
4: Deep and large cracks (at least 1 mm and less than 3 mm)
5: Cracks of at least 3 mm or severing likely to occur Note that in a situation in which cracks were not observed, an evaluation of "no cracks" was given. The results of this evaluation are shown in Tables 4 and 5.

<Discoloration>

After each of the test pieces had been subjected to the ozone degradation test described above, surface discoloration of the test piece was visually evaluated using the following four-level scale. The results of this evaluation are shown in Tables 4 and 5.

$A^+$: Black and glossy
A: Black but not glossy
$A^-$: Surface discoloration confirmed
F: Discoloration of entire surface

TABLE 4

| | Example 1 | Example 2 | Example 3 | Example 4 | Example 5 | Example 6 | Example 7 | Example 8 | Example 9 | Example 10 | Example 11 |
| --- | --- | --- | --- | --- | --- | --- | --- | --- | --- | --- | --- |
| Formulation | 1 | 2 | 2 | 2 | 2 | 2 | 2 | 2 | 2 | 2 | 2 |
| Bisanilino compound X | 1 | 0.2 | 1 | 3 | 6 | 10 | 3 | 1.5 | 1.5 | — | — |
| Bisanilino compound Y | — | — | — | — | — | — | — | — | — | 3 | — |
| Bisanilino compound Z | — | — | — | — | — | — | — | — | — | — | 3 |
| Anti-aging agent 6PPD | — | — | — | — | — | — | — | 1.5 | 1.5 | — | — |

TABLE 4-continued

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Anti-aging agent TMQ | 0.3 | — | — | — | — | — | 1 | — | 1 | — | — |
| Ozone resistance | A-2 | B-4 | A-4 | A-1 | No cracks | No cracks | No cracks | A-2 | A-1 | A-2 | A-2 |
| Discoloration | A+ | A+ | A+ | A+ | A | A− | A+ | A | A | A+ | A |

TABLE 5

|  | Comparative Example 1 | Comparative Example 2 | Comparative Example 3 | Comparative Example 4 | Comparative Example 5 | Comparative Example 6 |
|---|---|---|---|---|---|---|
| Formulation | 1 | 2 | 2 | 2 | 2 | 2 |
| Bisanilino compound X | — | — | — | — | — | — |
| Bisanilino compound Y | — | — | — | — | — | — |
| Bisanilino compound Z | — | — | — | — | — | — |
| Anti-aging agent 6PPD | 1 | 1 | 3 | 6 | 10 | 3 |
| Anti-aging agent TMQ | 0.3 | — | — | — | — | 1 |
| Ozone resistance | B-3 | B-4 | A-3 | A-2 | A-1 | A-2 |
| Discoloration | A | A | A− | F | F | A− |

From Tables 4 and 5, it can be seen that in the case of rubber compositions that contained the bisanilino compound represented by formula (I) blended with at least one rubber component selected from natural rubber and diene-based synthetic rubbers, and also in the case of rubber compositions according to the present disclosure that contained another anti-aging agent in combination with the bisanilino compound represented by formula (I), weather resistance was improved and surface discoloration was inhibited compared to rubber compositions that only contained conventional anti-aging agents.

The invention claimed is:

1. A rubber composition comprising
at least one rubber component selected from natural rubber and diene-based synthetic rubbers and, blended therewith, at least one bisanilino compound represented by formula (I) shown below

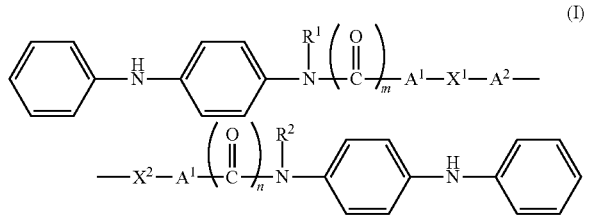

where, in formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom or an $—NR^3—$ group, and $X^2$ represents an oxygen atom or an $—NR^4—$ group, where $R^3$ and $R^4$ each represent a hydrogen atom or an alkyl group having a carbon number of 1-4, or collectively form an alkylene group having a carbon number of 1-4.

2. The rubber composition of claim 1, wherein
in the at least one bisanilino compound represented by formula (I), $R^1$ and $R^2$ are each, independently of one another, an alkyl group having a carbon number of 3-6, m and n are each 0, $A^1$ is an alkylene group having a carbon number of 1-4, $A^2$ is an alkylene group having a carbon number of 5-8, and $X^1$ and $X^2$ are each an oxygen atom.

3. The rubber composition of claim 1, wherein
a blending amount of the at least one bisanilino compound represented by formula (I) is in a range of from 0.2 parts by mass to 10 parts by mass relative to 100 parts by mass of the at least one rubber component.

4. A tire comprising a tire member comprising the rubber composition of claim 1.

5. The tire of claim 4, wherein
the tire member is either or both of a tread and a sidewall.

6. A bisanilino compound represented by formula (I) shown below

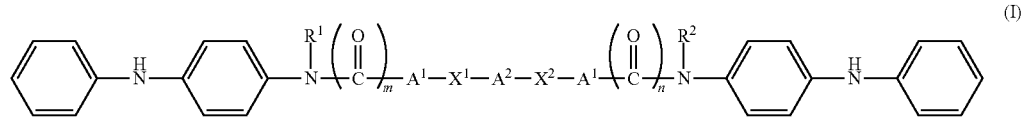 (I)

where, in formula (I), $R^1$ and $R^2$ each represent, independently of one another, a hydrogen atom or an alkyl group having a carbon number of 1-6, m and n each represent an integer of 0 or 1, $A^1$ represents an alkylene group having a carbon number of 1-7, $A^2$ represents an alkylene group having a carbon number of 1-8, $X^1$ represents an oxygen atom or an —$NR^3$— group, and $X^2$ represents an oxygen atom or an —$NR^4$— group, where $R^3$ and $R^4$ each represent a hydrogen atom or an alkyl group having a carbon number of 1-4, or collectively form an alkylene group having a carbon number of 1-4.

7. An anti-aging agent for natural rubber and diene-based synthetic rubber-use comprising the bisanilino compound of claim 6.

* * * * *